US011821822B2

(12) United States Patent
Huang et al.

(10) Patent No.: US 11,821,822 B2
(45) Date of Patent: Nov. 21, 2023

(54) METHODS, APPARATUSES AND SYSTEMS FOR LIQUID SUBSTANCE VAPORIZATION AND CONCENTRATION LEVEL DETERMINATION

(71) Applicant: Honeywell International Inc., Charlotte, NC (US)

(72) Inventors: Chuang Huang, Charlotte, NC (US); Li Liu, Charlotte, NC (US); Yawei Zhang, Charlotte, NC (US); Guidi Li, Charlotte, NC (US)

(73) Assignee: Honeywell International Inc., Charlotte, NC (US)

( * ) Notice: Subject to any disclaimer, the term of this patent is extended or adjusted under 35 U.S.C. 154(b) by 34 days.

(21) Appl. No.: 17/452,923

(22) Filed: Oct. 29, 2021

(65) Prior Publication Data

US 2022/0170830 A1    Jun. 2, 2022

(30) Foreign Application Priority Data

Nov. 30, 2020   (CN) .......................... 202011370115.1

(51) Int. Cl.
*G01N 1/44* (2006.01)
*G01N 1/24* (2006.01)
*G01N 1/14* (2006.01)

(52) U.S. Cl.
CPC ................. *G01N 1/24* (2013.01); *G01N 1/14* (2013.01); *G01N 1/44* (2013.01)

(58) Field of Classification Search
CPC .. G01N 1/24; G01N 1/14; G01N 1/44; G01N 33/0011; G01N 2001/2893; G01N 33/0006; G01N 27/64; G01N 33/0004; G01N 2001/149

USPC .......... 73/61.43, 61.56, 61.59, 61.77, 64.56, 73/863.11, 863.12, 864.72, 864.02; 422/530, 535

See application file for complete search history.

(56) References Cited

U.S. PATENT DOCUMENTS 4,732,046 A * 3/1988 Lawrence ............ G01N 1/4022
                                                        250/282
9,675,922 B2   6/2017 Ryan et al.
2012/0071362 A1   3/2012 Nhan et al.

FOREIGN PATENT DOCUMENTS

CN    207561268    *  7/2018
CN    108371566    *  8/2018
CN    113049759    *  6/2021

OTHER PUBLICATIONS

Semmens, Michael J. et al., "Using a Microporous Hollow-Fiber Membrane to Separate VOCs from Water", Apr. 1, 1989, Journal AWWA, Abstract, 81(4).

* cited by examiner

*Primary Examiner* — Robert R Raevis
(74) *Attorney, Agent, or Firm* — Alston & Bird LLP (57) ABSTRACT

Example methods and apparatuses for liquid substance vaporization and concentration level determination are provided. An example apparatus may include a constant temperature chamber having a vaporization housing that includes a capillary component disposed within and a syringe assembly configured to inject a liquid substance to the capillary component. An example method may include determining an injection rate for injecting the liquid substance to the capillary component, determining a flow rate of the gaseous substance in the vaporization housing, and calculating a concentration level of a vaporized substance based on the injection rate and the flow rate.

20 Claims, 5 Drawing Sheets

METHODS, APPARATUSES AND SYSTEMS FOR LIQUID SUBSTANCE VAPORIZATION AND CONCENTRATION LEVEL DETERMINATION

CROSS-REFERENCE TO RELATED APPLICATIONS

This application claims priority pursuant to 35 U.S.C. 119(a) to China Patent Application No. 202011370115.1, filed Nov. 30, 2020, which application is incorporated herein by reference in its entirety.

BACKGROUND

A gas detector is a device that may sense and/or detect the presence of gas(es) in an area. For example, a gas detector may be installed in a work environment (such as, but not limited to, in an oil platform/offshore drilling rig), and may be configured to detect the presence of hazardous, toxic, flammable and/or combustible gas(es), such as, but not limited to, sulfur dioxide ($SO_2$), hydrogen sulfide ($H_2S$), or carbon monoxide (CO). However, many methods, apparatuses, and systems related to gas detectors are plagued by technical challenges and limitations.

BRIEF SUMMARY

Various embodiments described herein relate to methods, apparatuses, and systems for vaporizing liquid substance and/or determining a concentration level of the vaporized substance.

In accordance with various embodiments of the present disclosure, an example apparatus for vaporizing a liquid substance is provided. The example apparatus may comprise an example constant temperature chamber and an example syringe assembly. In some embodiments, the example constant temperature chamber may comprise an example vaporization housing. In some embodiments, an example capillary component may be disposed in the example vaporization housing. In some embodiments, the example syringe assembly may be configured to inject the liquid substance to the example capillary component.

In some embodiments, the example vaporization housing may comprise an example input tunnel and an example output tunnel. In some embodiments, the example input tunnel may be configured to receive a gaseous substance. In some embodiments, the example output tunnel may be configured to discharge a vaporized substance.

In some embodiments, the example syringe assembly may comprise an example injection component. In some embodiments, a first end of the example injection component may be inserted in the example capillary component.

In some embodiments, the example syringe assembly may comprise an example barrel component. In some embodiments, the example barrel component may store the liquid substance.

In some embodiments, the example syringe assembly may comprise an example plunger component. In some embodiments, the example plunger component may comprise an example plunger flange element.

In some embodiments, the example apparatus may comprise an example carriage component that may be in contact with the example plunger flange element of the example plunger component. In some embodiments, the example apparatus may comprise an example lead screw assembly coupled to the example carriage component.

In some embodiments, the example lead screw assembly may comprise an example nut component having inner threads. In some embodiments, the example lead screw assembly may comprise an example shaft component having outer threads that engage with the inner threads of the example nut component. In some embodiments, the example carriage component may be fastened to the example nut component. In some embodiments, the example carriage component may be slidably coupled to an example rail component.

In some embodiments, the example lead screw assembly may comprise an example motor component coupled to the example shaft component. In some embodiments, the example motor component may be configured to exert rotational force on the example shaft component. In some embodiments, the example lead screw assembly may comprise an example processing circuitry in electronic communication with the example motor component.

In some embodiments, the example apparatus may comprise an example air pump component coupled to the example input tunnel of the example vaporization housing. In some embodiments, the example apparatus may comprise an example flow rate controller component coupled to the example output tunnel of the example vaporization housing. In some embodiments, the example apparatus may comprise an example processing circuitry in electronic communication with the example flow rate controller component.

In some embodiments, the example apparatus may comprise an example compressed air storage component coupled to the example input tunnel of the example vaporization housing. In some embodiments, the example apparatus may comprise an example flow rate controller component coupled to the example output tunnel of the example vaporization housing. In some embodiments, the example output tunnel may comprise at least one example decompression aperture. In some embodiments, the example apparatus may comprise an example processing circuitry in electronic communication with the example flow rate controller component.

In some embodiments, the example capillary component may comprise acetate fiber material. In some embodiments, the example capillary component may comprise glass fiber material. In some embodiments, the example capillary component may comprise paper material.

In accordance with various embodiments of the present disclosure, an example method for determining a concentration level of a vaporized substance is provided. The example method may comprise determining an injection rate of injecting an example liquid substance to an example capillary component, determining a flow rate of an example gaseous substance for vaporizing the liquid substance in a vaporization housing, and calculating the concentration level of the example vaporized substance based on the injection rate and the flow rate. In some embodiments, the example capillary component is disposed in an example vaporization housing.

In some embodiments, the example method may comprise causing an example syringe assembly to inject the example liquid substance to the example capillary component. In some embodiments, the example syringe assembly may comprise an example injection component, and a first end of the example injection component may be inserted in the example capillary component. In some embodiments, the example syringe assembly may comprise an example barrel component storing the example liquid substance. In some embodiments, the example syringe assembly may comprise an example plunger component. In some embodiments, the example plunger component may comprise an example plunger flange element.

In some embodiments, the example plunger flange element may be in contact with an example carriage component. In some embodiments, the example carriage component may be coupled to an example lead screw assembly.

In some embodiments, the example lead screw assembly may comprise an example nut component having inner threads. In some embodiments, the example lead screw assembly may comprise an example shaft component having outer threads that engage with the inner threads of the example nut component. In some embodiments, the example carriage component may be fastened to the example nut component. In some embodiments, the example carriage component may be slidably coupled to an example rail component.

In some embodiments, the example lead screw assembly may comprise an example motor component coupled to the example shaft component. In some embodiments, the example motor component may be configured to exert rotational force on the example shaft component.

In some embodiments, determining the injection rate for injecting the example liquid substance may comprise determining a motor speed of the example motor component.

In some embodiments, determining the flow rate of the example gaseous substance may comprise receiving a flow rate reading indication from an example flow rate controller component coupled to an example output tunnel of the example vaporization housing.

In some embodiments, the example vaporization housing may be disposed in an example constant temperature chamber.

In some embodiments, the example capillary component may comprise acetate fiber material. In some embodiments, the example capillary component may comprise glass fiber material.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which.

DETAILED DESCRIPTION OF THE INVENTION

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

The phrases "in one embodiment," "according to one embodiment," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such component or feature may be optionally included in some embodiments, or it may be excluded.

The term "electronically coupled" or "in electronic communication with" in the present disclosure refer to two or more electrical elements (for example, but not limited to, an example processing circuitry, an example motor component, an example flow rate controller component) and/or electric circuit(s) being connected through wired means (for example but not limited to, conductive wires or traces) and/or wireless means (for example but not limited to, wireless network, electromagnetic field), such that data and/or information (for example, electronic indications, signals) may be transmitted to and/or received from the electrical elements and/or electric circuit(s) that are electronically coupled.

As described above, many methods, apparatuses, and systems related to gas detectors are plagued by technical challenges and limitations.

For example, many gas detectors require periodic calibration to ensure correctness and accuracy of reading from these gas detectors, as well as integrity of system(s) that the gas detector(s) may be part(s) of. Many methods and systems for calibrating a gas detector require a calibration substance in a gaseous state (also referred to as "calibration gas") having a predetermined concentration level. As an example, calibrating a $SO_2$ detector may involve providing calibration gas that comprises $SO_2$ in a predetermined concentration level to the $SO_2$ detector, and adjusting readings from the $SO_2$ detector based on the predetermined concentration level.

However, many calibration substances may not be stored and/or transported in a gaseous state and may need to be vaporized into a gaseous state so that a calibration may be conducted.

As an example, hydrogen peroxide ($H_2O_2$) having a predetermined concentration level (also referred to as "calibration $H_2O_2$") may be stored in a liquid state (for example, at room temperature), while calibrating a $H_2O_2$ detector may require the calibration $H_2O_2$ to be in a gaseous state. Many calibration methods and calibration systems may vaporize the calibration $H_2O_2$ from a liquid state to a gaseous state.

As another example, a photoionization detector (PID) is a gas detector that may measure the concentration level of volatile organic compounds in a gaseous substance. The term "volatile organic compound" (or "VOC") refers to organic compounds that may have a high vapor pressure at ordinary room temperature (i.e. they may easily become gases or vapors). Example chemicals in example volatile organic compounds may include, for example, formaldehyde, methane, and benzene. Calibrating a PID may require a calibration substance having a predetermined concentration level of VOC, and such a calibration substance may be stored in a liquid state.

Some calibration methods and calibration systems may vaporize a calibration substance from a liquid state to a gaseous state through a heating process. For example, some calibration systems may comprise a tube or a vessel that stores the calibration substance and a heater component (such as a heating coil) that may increase the temperature of the tube or vessel. Some calibration systems may also comprise a stirring component (for example, a stirring rod) that may cause movement of the calibration substance within the tube or vessel, which may increase the vaporization rate of converting the calibration substance from a liquid state to a gaseous state.

However, calibration methods and calibration systems that implement a heating process may fall short in providing accurate calibration of gas detectors. For example, the heating component implemented by these calibration methods and calibration systems may fail to provide a constant temperature, therefore causing fluctuations in the vaporization rate of converting the calibration substance from a liquid state to a gaseous state. As a result, the calibration substance (in the gaseous state) that is obtained through the heating process may have an actual concentration level that varies from the predetermined concentration level of the calibration substance (in the gaseous state). The lack of stability of concentration level in the calibration substance (in the gaseous state) may cause the gas detector to be erroneously calibrated and provide inaccurate readings.

In addition, many calibration substances may be unstable, flammable and/or combustible, and a heating process may not be suitable for converting such calibration substance from a liquid state to a gaseous state. For example, $H_2O_2$ may lose stability rapidly when it is heated, and may become unstable. The rapid loss of stability may cause a pressure increase, which may in turn cause explosion or rupture of the tube or vessel where $H_2O_2$ is stored. Further, heating $H_2O_2$ may cause it to be decomposed into water and oxygen. When oxygen is accumulated to a certain level and mixed with an open flame, an explosion may occur. As such, vaporizing $H_2O_2$ through a heating process to produce calibration substance may not only cause incorrect calibration of gas detectors, but also create safety hazards.

Some calibration methods and calibration systems may vaporize a calibration substance from a liquid state to a gaseous state through a grinding or milling process. For example, some calibration systems may comprise a mortar component and a pestle component. The calibration substance (in a liquid state) may be disposed in the mortar component, and the pestle component may be in contact with the calibration substance in the mortar component. In some examples, the pestle component may stir and/or cause rotational motion of the calibration substance, so as to increase a surface area of the calibration substance to facilitate vaporization.

However, calibration methods and calibration systems implementing a grinding or milling process similarly fail to provide a calibration substance having a stable concentration level. For example, while the surface area of the calibration substance may be increased through the grinding or milling process, the vaporization rate of the calibration substance may be only marginally increased. The slow vaporization rate may cause such calibration methods and calibration systems to produce gaseous calibration substance with inconsistent concentration level and with low efficiency. Further, such calibration systems and calibration methods may require the mortar component and the pestle component to operate in a closed or sealed environment to prevent leakage of the gaseous calibration substance, which may further complicate manufacturing process of such calibration systems and limiting applicability of such calibration methods.

Some calibration methods and calibration systems may determine a concentration level of gaseous calibration substance based on measuring a weight loss of the calibration substance in the liquid state from before vaporization to after vaporization. However, such calibration methods and calibration systems can be time consuming in determining the concentration level, as they require a long passage of time for the calibration substance to be sufficiently vaporized so as to create a measurable weight loss. Such calibration methods and calibration systems may also fail to produce calibration substance having a required concentration level because the amount of the calibration substance is limited to the size of the tube or the vessel storing the calibration substance. In situations where the amount of the calibration substance stored in the tube or the vessel is less than the amount needed for reaching the required concentration level, the resultant vaporized calibration substance may not meet the calibration requirements for many gas detector(s).

Further, the tube/vessel implemented by many calibration methods and calibration systems may comprise glass material, which may absorb vaporized substance (such as, but not limited to, vaporized $H_2O_2$). As such, these calibration methods and calibration systems are not suitable for vaporizing substances such as $H_2O_2$.

In contrast, various embodiments of the present disclosure may overcome technical challenges and limitations related to gas detectors. In some embodiments, a substance (in a liquid state) may be diffused in a capillary component (such as, but not limited to, acetate fiber). For example, a syringe assembly may be configured to inject the substance to the capillary component at an injection rate. The capillary component may expand a surface area of the substance and facilitate vaporization of the substance. In some embodiments, the capillary component may be exposed to a flow of gaseous substance having a flow rate, which may move atoms or molecules of the substance from the surface of the capillary component into air and therefore converting the substance from a liquid state to a gaseous state. In some embodiments, the concentration level of the vaporized substance may be determined based on the injection rate and the flow rate, details of which are described herein.

As such, various embodiments of present disclosure may provide apparatuses, methods, and systems for vaporizing a substance from a liquid state to a gaseous state and/or providing a vaporized substance with a stable concentration level. In some embodiments, the vaporized substance may be provided to calibrate a substance sensing component (such as, but not limited to, gas detector(s)). Various embodiments of the present disclosure may provide more flexibility and require less time and cost in producing vaporized substance than many other systems and methods, details of which are described herein.

Figure 1:
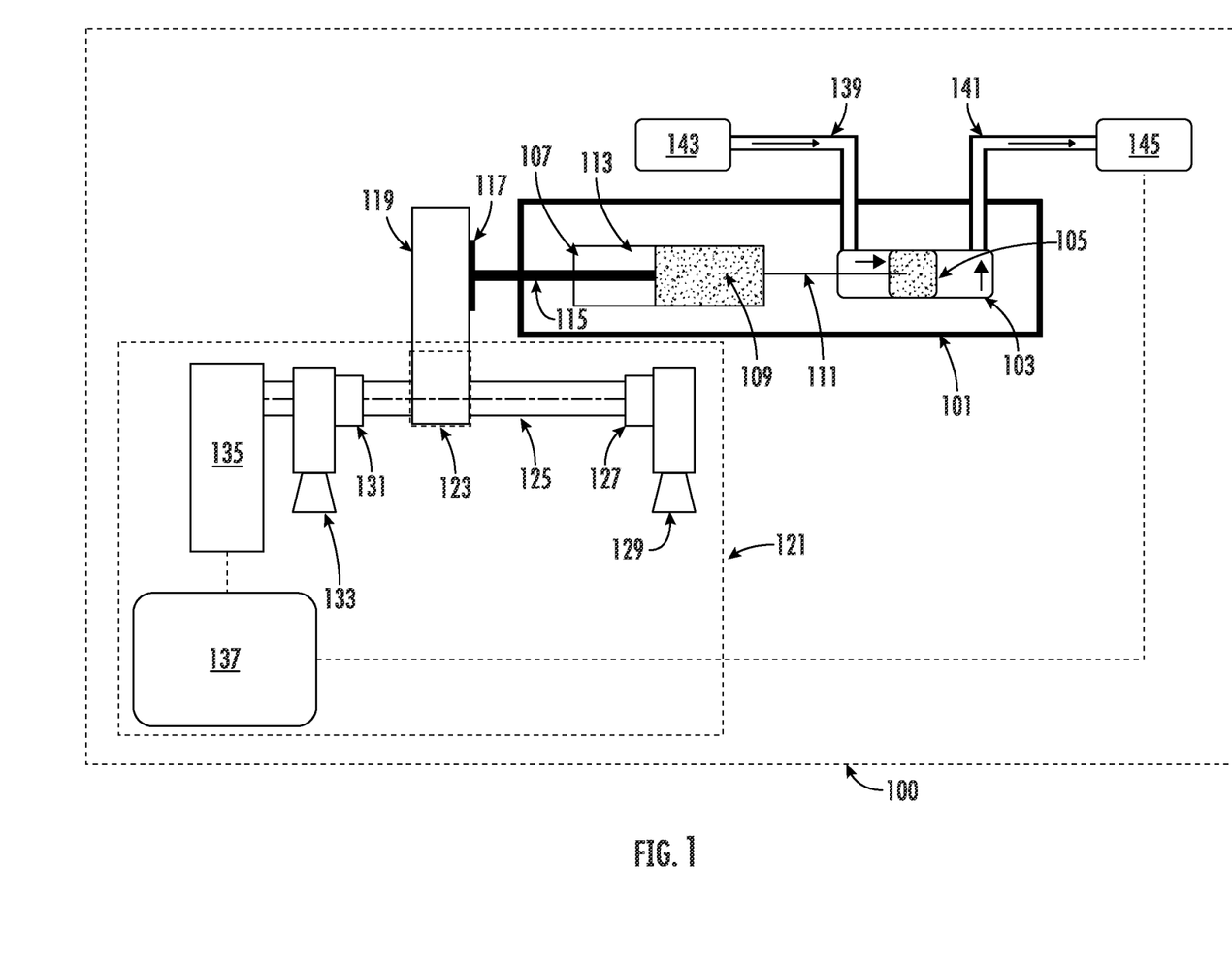
FIG. 1 illustrates an example system structure diagram in accordance with various embodiments of the present disclosure.

Referring now to FIG. 1, an example system structure diagram illustrating various example components of an example liquid substance vaporization system 100 in accordance with various embodiments of the present disclosure is shown. In some embodiments, the example liquid substance vaporization system 100 is also referred to as an example liquid substance vaporization apparatus. In some embodiments, the example liquid substance vaporization apparatus/system is for vaporizing a liquid substance.

In the example shown in FIG. 1, the example liquid substance vaporization system 100 comprises an example constant temperature chamber 101.

In some embodiments, the example constant temperature chamber 101 may comprise a plurality of walls or sides forming a structure or an enclosure that houses one or more components and/or elements of the example liquid substance vaporization system 100. For example, the example constant temperature chamber 101 may comprises six sides forming a cuboid shape, where one or more other components and/or elements of the example liquid substance vaporization system 100 are disposed within the cuboid shape (such as, but not limited to, an example vaporization housing 103, an example injection component 111 of an example syringe assembly 107, and/or an example barrel component 113 of an example syringe assembly 107).

In some embodiments, one or more walls or sides of the example constant temperature chamber 101 may comprise thermal insulation material. The term "thermal insulation material" in the present disclosure refers to a material or substance that has a thermal conductivity lower than a predetermined thermal conductivity threshold. The term "thermal conductivity" in the present discourse refers to a measure of a material to transfer heat. In particular, heat transfer may occur at a faster rate in materials that have high thermal conductivity than in materials that have low thermal conductivity. As such, the thermal insulation material of the one or more walls or sides of the example constant temperature chamber 101 may reduce and/or limit heat loss from within the example constant temperature chamber 101, and may reduce and/or limit temperature fluctuation that may affect the vaporization rate of the substance and/or the concentration level of the vaporized substance. In some embodiments, the thermal insulation material of the one or more walls or sides of the example constant temperature chamber 101 may comprise material(s) such as, but not limited to, polytetrafluoroethylene (PTFE), polystyrene, polyisocyanurate, and/or the like.

While the description above provides an example of a constant temperature chamber, it is noted that the scope of the present disclosure is not limited to the description above. In some examples, an example constant temperature chamber may comprise walls or sides forming other shapes, including, but not limited to, a cube shape, a sphere shape, and/or the like.

In some examples, an example constant temperature chamber may comprise one or more additional and/or alternative elements, and/or may be in other forms. For example, an example constant temperature chamber may be in the form of an environmental chamber (also referred to as a "climate chamber" or an "environmental test chamber") that is configured to provide a housing or an enclosure that has a constant environmental temperature. In such an example, the environmental chamber may comprise an opening (for example, a door) through which various components and/or elements of the example liquid substance vaporization system 100 may be disposed within the environmental chamber.

As described above, the example constant temperature chamber 101 may house one or more other components and/or elements of the example liquid substance vaporization system 100. In the example shown in FIG. 1, the example constant temperature chamber 101 may comprise an example vaporization housing 103 that is disposed in the example constant temperature chamber 101.

In some embodiments, the example vaporization housing 103 may comprise a plurality of walls or sides forming a structure or an enclosure that houses one or more other components and/or elements of the example liquid substance vaporization system 100, such as, but not limited to, an example capillary component 105. For example, the example vaporization housing 103 may comprises six sides forming a cuboid shape, where the example capillary component 105 is disposed within the cuboid shape of the example vaporization housing 103.

In some embodiments, one or more walls or sides of the example vaporization housing 103 may comprise thermal insulation material. As described above, the thermal insulation material may have a thermal conductivity that is lower than a predetermined thermal conductivity threshold. For example, heat transfer may occur at a slower rate in the thermal insulation material than in materials that have a high thermal conductivity. As such, the thermal insulation material of the one or more walls or sides of the example vaporization housing 103 may reduce and/or limit heat loss from within the example vaporization housing 103, and may reduce and/or limit temperature fluctuation that may affect the vaporization rate of the substance and/or the concentration level of the vaporized substance. In some embodiments, the thermal insulation material of the one or more walls or sides of the example vaporization housing 103 may comprise material(s) such as, but not limited to, polytetrafluoroethylene (PTFE), polystyrene, polyisocyanurate, and/or the like.

While the description above provides an example of a vaporization housing, it is noted that the scope of the present disclosure is not limited to the description above. In some examples, an example vaporization housing may comprise walls or sides forming other shapes, including, but not limited to, a cube shape, a sphere shape, and/or the like.

In some examples, an example vaporization housing may comprise one or more additional and/or alternative elements, and/or may be in other forms. For example, an example vaporization housing may be in the form of a tube or tubing, such as, but not limited to, a PTFE tubing. In such an example, the PTFE tubing may comprise PTFE material in the form of a tube, and the example capillary component 105 is disposed within tube.

As described above, the example capillary component 105 may be disposed in the example vaporization housing 103. In the present disclosure, the example capillary component 105 comprises material or materials that may diffuse or disperse a liquid substance when the liquid substance is in contact with, injected to, and/or absorbed by such material or materials, and/or may expand a surface area of the liquid substance.

In some embodiments, the example capillary component 105 may comprise material or materials that may provide capillary effect or capillary action on the liquid substance that is in contact with, injected to, and/or absorbed by such material or materials. The terms "capillary effect" and "capillary action" refer to the ability of a material to draw liquid substance to flow or expand through part(s) or all of the material without the assistance of (or, in some example, even in opposition to) an external force. As such, the example capillary component 105 may increase the vaporization rate of the liquid substance. In some embodiments, materials that may provide capillary effect or capillary action may include porous materials such as, but not limited to, paper material (such as filter paper material), nonwoven fabric material, and/or the like. In some embodiments, materials that may provide capillary effect or capillary action may include non-porous materials or less-porous materials such as, but not limited to, acetate fiber material, polyester fiber material, glass fiber material, and/or the like.

For example, the example capillary component 105 may comprise acetate fiber material. In some embodiments, the acetate fiber material of the example capillary component 105 may diffuse or disperse a liquid substance when the liquid substance is in contact with, injected to, and/or absorbed by the acetate fiber material, and/or may expand the surface area of the liquid substance. In some embodiments, the acetate fiber material of the example capillary component 105 may provide capillary effect or capillary action on the liquid substance. In some embodiments, the acetate fiber material of the example capillary component 105 may increase the vaporization rate of the liquid substance.

Additionally, or alternatively, the example capillary component 105 may comprise glass fiber material. In some embodiments, the glass fiber material of the example capillary component 105 may diffuse or disperse a liquid substance when the liquid substance is in contact with, injected to, and/or absorbed by the glass fiber material, and/or may expand the surface area of the liquid substance. In some embodiments, the glass fiber material of the example capillary component 105 may provide capillary effect or capillary action on the liquid substance. In some embodiments, the glass fiber material of the example capillary component 105 may increase the vaporization rate of the liquid substance.

Additionally, or alternatively, the example capillary component 105 may comprise paper material. In some embodiments, the paper material of the example capillary component 105 may diffuse or disperse a liquid substance when the liquid substance is in contact with, injected to, and/or absorbed by the acetate fiber material, and/or may expand the surface area of the liquid substance. In some embodiments, the paper material of the example capillary component 105 may provide capillary effect or capillary action on the liquid substance. In some embodiments, the paper material of the example capillary component 105 may increase the vaporization rate of the liquid sub stance.

While the description above provides some example materials for the example capillary component, it is noted that the scope of the present disclosure is not limited to the description above. In some examples, an example capillary component may comprise one or more additional and/or alternative material(s).

As described above, in some embodiments, a liquid substance may be in contact with, injected to, and/or absorbed by the example capillary component 105. In the example shown in FIG. 1, the example liquid substance vaporization system 100 comprises an example syringe assembly 107. In some embodiments, the example syringe assembly 107 is configured to inject a liquid substance 109 to the example capillary component 105.

In the present disclosure, a syringe assembly refers to a type of reciprocating pump that moves, conveys, or transports a liquid substance (for example, moving, conveying, or transporting the liquid substance into the example capillary component 105). In the example shown in FIG. 1, the example syringe assembly 107 may comprise an example injection component 111, an example barrel component 113, and/or an example plunger component 115.

In some embodiments, the example barrel component 113 is in the form of a cylindrical tube. For example, the example barrel component 113 may comprise an opening on one end for receiving the example plunger component 115, and may comprise a discharge orifice on the other end for take in or expel the liquid substance 109, details of which are described herein. In some embodiments, the example barrel component 113 stores the liquid substance 109 (for example, in the cylindrical tube), and the liquid substance 109 is to be vaporized by the example liquid substance vaporization system 100.

In some embodiments, the example barrel component 113 may comprise material or materials such as, but not limited to, acrylonitrile butadiene styrene (ABS), polyvinyl chloride (PVC), chlorinated polyvinyl chloride (CPVC), polyethylene (PE), polybutylene (PB), fiber reinforced plastic (FRP), polypropylene (PP), and/or the like.

In some embodiments, the material or materials of the example barrel component 113 may be determined based on material compatibility with the liquid substance 109. For example, the material of the example barrel component 113 may be selected such that the example barrel component 113 is resistant to corrosion, rust and/or stains when it comes in contact with and/or stores the liquid substance 109.

In some embodiments, the example barrel component 113 may comprise glass material. In some embodiments, when the liquid substance 109 comprises $H_2O_2$, glass material may not be suitable for the example barrel component 113 because $H_2O_2$ may react with glass material and yield sodium hydroxide. In such embodiments, the example barrel component 113 may comprise material(s) such as, but not limited to, PE, stainless steel, and/or the like, which are compatible with $H_2O_2$.

In some embodiments, the example liquid substance vaporization system 100 may comprise a plurality of barrel components, each storing a different kind/type of liquid substance. As such, the example liquid substance vaporization system 100 allows vaporizing different liquid substances by swapping or replacing the installed barrel component with a corresponding barrel component storing the liquid substance to be vaporized.

In the example shown in FIG. 1, one end of the example plunger component 115 of the example syringe assembly 107 may be inserted in the example barrel component 113 (for example, through the opening of the cylindrical tube of the example barrel component 113 described above). In some embodiments, the example plunger component 115 may be linearly pulled and pushed along the inside of the example barrel component 113. In some embodiments, the example plunger component 115 may be pulled and/or pushed through an opening of a side wall of the example constant temperature chamber 101.

In some embodiments, when the example plunger component 115 is pulled, the example syringe assembly 107 may take in the liquid substance 109 (for example, through the discharge orifice of the cylindrical tube of the example barrel component 113 described above) and store the liquid substance 109 in the example barrel component 113. In some embodiments, when the example plunger component 115 is pushed, the example syringe assembly 107 may expel the liquid substance 109 that is stored in the example barrel component 113 (for example, through the discharge orifice of the cylindrical tube of the example barrel component 113 described above).

As described above, the example syringe assembly 107 may comprise an example injection component 111. In some embodiments, one end of the example injection component 111 of the example syringe assembly 107 may be connected to the example barrel component 113. For example, a first end of the example injection component 111 may be connected to or fitted with the discharge orifice of the cylindrical tube of the example barrel component 113 described above. As such, when the example plunger component 115 is pulled, the example syringe assembly 107 may take in the liquid substance 109 through the example injection component 111. When the example plunger component 115 is pushed, the example syringe assembly 107 may expel the liquid substance 109 through the example injection component 111.

In some embodiments, one end (for example, a second end) of the example injection component 111 of the example syringe assembly 107 may be inserted in the example capillary component 105. For example, the example injection component 111 may be positioned through an aperture of a side wall of the example vaporization housing 103, and a tip of the example injection component 111 may be inserted in the example capillary component 105. As such, when the example plunger component 115 is pushed, the example syringe assembly 107 may move, convey, or transport the liquid substance 109 from the example barrel component 113 to the example capillary component 105 through the example injection component 111.

In various embodiments of the present disclosure, the example injection component 111 may be in various forms. In some embodiments, the example injection component 111 may be in the form of a needle comprising material(s) such as, but not limited to, nickel, carbon steel, and/or the like. Additionally, or alternatively, the example injection component 111 may be in the form of a nozzle comprising material(s) such as, but not limited to, cooper, stainless steel, and/or the like. Additionally, or alternatively, the example injection component 111 may be in the form of a tubing comprising material(s) such as, but not limited to, PTFE, PVC, ABS, and/or the like.

In some embodiments, the material or materials of the example injection component 111 may be determined based on material compatibility with the liquid substance 109. For example, the material of the example injection component 111 may be selected such that the example injection component 111 is resistant to corrosion, rust and/or stains when it comes in contact with and/or conveys the liquid substance 109. For example, when the liquid substance 109 comprises $H_2O_2$, the example injection component 111 may comprise material(s) such as, but not limited to, stainless steel.

As described above, the example plunger component 115 may be linearly pulled and pushed along the inside of the example barrel component 113. In some embodiments, the example plunger component 115 comprises an example plunger flange element 117 that is disposed on one end of the plunger component 115 (and the other end of the plunger component 115 may be inserted in the example barrel component 113 as described above). In some embodiments, the pull motion and/or the push motion of the example plunger component 115 may be triggered or caused by an example carriage component 119 that is in contact with the example plunger flange element 117, and/or by an example lead screw assembly 121 that is coupled to the example carriage component 119.

In some embodiments, the example lead screw assembly 121 may comprise an example nut component 123 and an example shaft component 125.

In some embodiments, the example nut component 123 may be in the form of a piece of metal (and/or other material) and may comprise a threaded hole having inner threads. In some embodiments, the example nut component 123 may be in a hexagonal shape. In some embodiments, the example nut component 123 may be in other shapes, including, but not limited to, a square shape.

In some embodiments, the example shaft component 125 may be in the form of a leadscrew (also referred to as a "power screw" or a "translation screw"). In some embodiments, the example shaft component 125 may comprise outer threads that engage and mate with the inner threads of the example nut component 123.

In some embodiments, the outer threads of the example shaft component 125 may comprise square threads. Additionally, or alternatively, the outer threads of the example shaft component 125 may comprise round threads. Additionally, or alternatively, the outer threads of the example shaft component 125 may comprise buttress threads. Additionally, or alternatively, the outer threads of the example shaft component 125 may comprise other type(s) of threads.

In the example shown in FIG. 1, a first end of the example shaft component 125 may be fitted to an example shaft support bearing component 127. In some embodiments, the shaft support bearing component 127 may be in the form of, for example but not limited to, a ball bearing.

For example, the ball bearing of the shaft support bearing component 127 may comprise an inner ring having a bore and an outer ring that is secured to a structure (for example, a support stand 129 that is not moveable as shown in FIG. 1). In some embodiments, the inner ring and the outer ring are separated by a plurality of rolling elements (for example, metal balls). In some embodiments, the first end of the example shaft component 125 may be inserted into the bore of the inner ring of shaft support bearing component 127. When rotational force is exerted on the example shaft component 125, the inner ring may rotate while the outer ring may be secured as it is separated from the inner ring.

In the example shown in FIG. 1, a second end of the example shaft component 125 may be fitted to an example shaft support bearing component 131 that is secured to a support stand 133. In some embodiments, the support stand 133 is not moveable. Similar to those described above in connection with the shaft support bearing component 127, in some embodiments, the shaft support bearing component 131 may be in the form of, for example but not limited to, a ball bearing. For example, the ball bearing of the shaft support bearing component 131 may comprise an inner ring having a bore and an outer ring that is secured to a structure (for example, the support stand 133). In some embodiments, the inner ring and the outer ring are separated by a plurality of rolling elements (for example, metal balls).

While the description above provides an example of shaft support bearing component in the form of ball bearing, it is noted that the scope of the present disclosure is not limited to the description above. In some examples, an example shaft support bearing component may comprise one or more additional and/or alternative elements, and/or may be in other form(s).

In some embodiments, the second end of the example shaft component 125 may be inserted into the bore of the inner ring of the shaft support bearing component 127 and through an aperture of the support stand 133. In some embodiments, the second end of the example shaft component 125 may be coupled to an example motor component 135. In some embodiments, the example carriage component 119 and the example lead screw assembly 121 may convert or translate rotational force (or motion) from the example motor component 135 to linear force (or motion).

In some embodiments, the example motor component 135 may be configured to convert electrical energy into mechanical energy. For example, the example motor component 135 may be connected to a power source element (for example, but not limited to, direct current (DC) sources, alternating current (AC) sources) that provides electrical energy. The example motor component 135 may convert the electrical energy into torque force through interactions between a magnetic field of the example motor component 135 and electric current in a wire winding of the example motor component 135. The example motor component 135 may exert the torque force on a shaft element of the example motor component 135. In some embodiments, the shaft element of the example motor component 135 may be coupled to the example shaft component 125. As such, the example motor component 135 is configured to exert rotational force on the example shaft component 125.

In some embodiments, the example motor component 135 may be in the form of a step motor (also referred to as "stepper motor") that may divide a full rotation into multiple segments or steps. By adjusting the timing for performing these segments or steps, a rotational speed of shaft element of the example motor component 135 (and the rotational speed of the example shaft component 125) may be controlled.

For example, as shown in FIG. 1, the lead screw assembly 121 may comprise an example processing circuitry 137 that is in electronic communication with the example motor component 135. The example processing circuitry 137 may execute one or more program instructions and cause the example motor component 135 to start and/or stop exerting rotational forces on the example shaft component 125, and/or adjusting the rotational speed of the example motor component 135 and the example shaft component 125.

While the description above provides an example of the motor component, it is noted that the scope of the present disclosure is not limited to the description above. In some examples, an example motor component may comprise one or more additional and/or alternative elements, and/or may be in other forms.

While the description above provides an example of the processing circuitry, it is noted that the scope of the present disclosure is not limited to the example above. In some embodiments, the processing circuitry may be in various forms and/or communicate with one or more other electric components.

For example, the example processing circuitry 137 (and/or co-processor or any other processing circuitry assisting or otherwise associated with the example processing circuitry 137) may be in communication with the example memory circuitry via a bus for passing data and/or information. The example memory circuitry is non-transitory and may include, for example, one or more volatile and/or non-volatile memories. In other words, for example, the example memory circuitry may be an electronic storage device (e.g., a computer-readable storage medium). The example memory circuitry may be configured to store information, data, content, applications, computer instructions, or the like for enabling the example processing circuitry 137 to carry out various functions in accordance with example embodiments of the present disclosure.

The example processing circuitry 137 may be embodied in a number of different ways and may, for example, include one or more processing devices configured to perform independently. In some examples, the example processing circuitry 137 may include one or more processors configured in tandem via a bus to enable independent execution of instructions, pipelining, and/or multithreading. The use of the term "processor" or "processing circuitry" may be understood to include a single core processor, a multi-core processor, multiple processors internal to the apparatus, and/or remote or "cloud" processors.

In some examples, the example processing circuitry 137 may be configured to execute instructions stored in the example memory circuitry or otherwise accessible to the example processing circuitry 137. In some examples, the example processing circuitry 137 may be configured to execute hard-coded functionalities. As such, whether configured by hardware or software methods, or by a combination thereof, the example processing circuitry 137 may represent an entity (e.g., physically embodied in circuitry) capable of performing operations according to an embodiment of the present disclosure while configured accordingly. Alternatively, as another example, when the example processing circuitry 137 may be embodied as an executor of computer instructions, and the computer instructions may specifically configure the example processing circuitry 137 to perform the algorithms and/or operations described herein when the instructions are executed.

Referring back to FIG. 1, the example carriage component 119 may be in various shapes and/or forms in various embodiments. For example, the example carriage component 119 may be in the shape of a rectangular block. As another example, the example carriage component 119 may be in the shape of a square block. As another example, the example carriage component 119 may be in other shapes. In some embodiments, the example carriage component 119 may comprise material having rigid characteristics, such as, but not limited to, high-density polyethylene (HDPE), metal, and/or the like.

In some embodiments, the example carriage component 119 may be fastened to the example nut component 123. In some embodiments, the example carriage component 119 may be fastened to the nut component 123 through, such as but not limited to, one or more fastening mechanisms and/or attaching mechanisms, including not limited to, mechanical means (for example, one or more mechanical fasteners or methods such as soldering, snap-fit, permanent and/or non-permeant fasteners), chemical means (for example, adhesive material such as glues), magnetic means (for example, through the use of magnet(s)), and/or suitable means. As an example, the example carriage component 119 may comprise a slot disposed on a bottom portion of the example carriage component 119. The slot may provide an opening that fits the example nut component 123. In this example, the example carriage component 119 may be fastened to the example nut component 123 through a snap-fit mechanism.

While the description above provides an example of fastening mechanism between the example carriage component 119 and the example nut component 123, it is noted that the scope of the present disclosure is not limited to the description above. For example, in some embodiments, the example carriage component 119 and the example nut component 123 may be an integral part.

Figure 2:
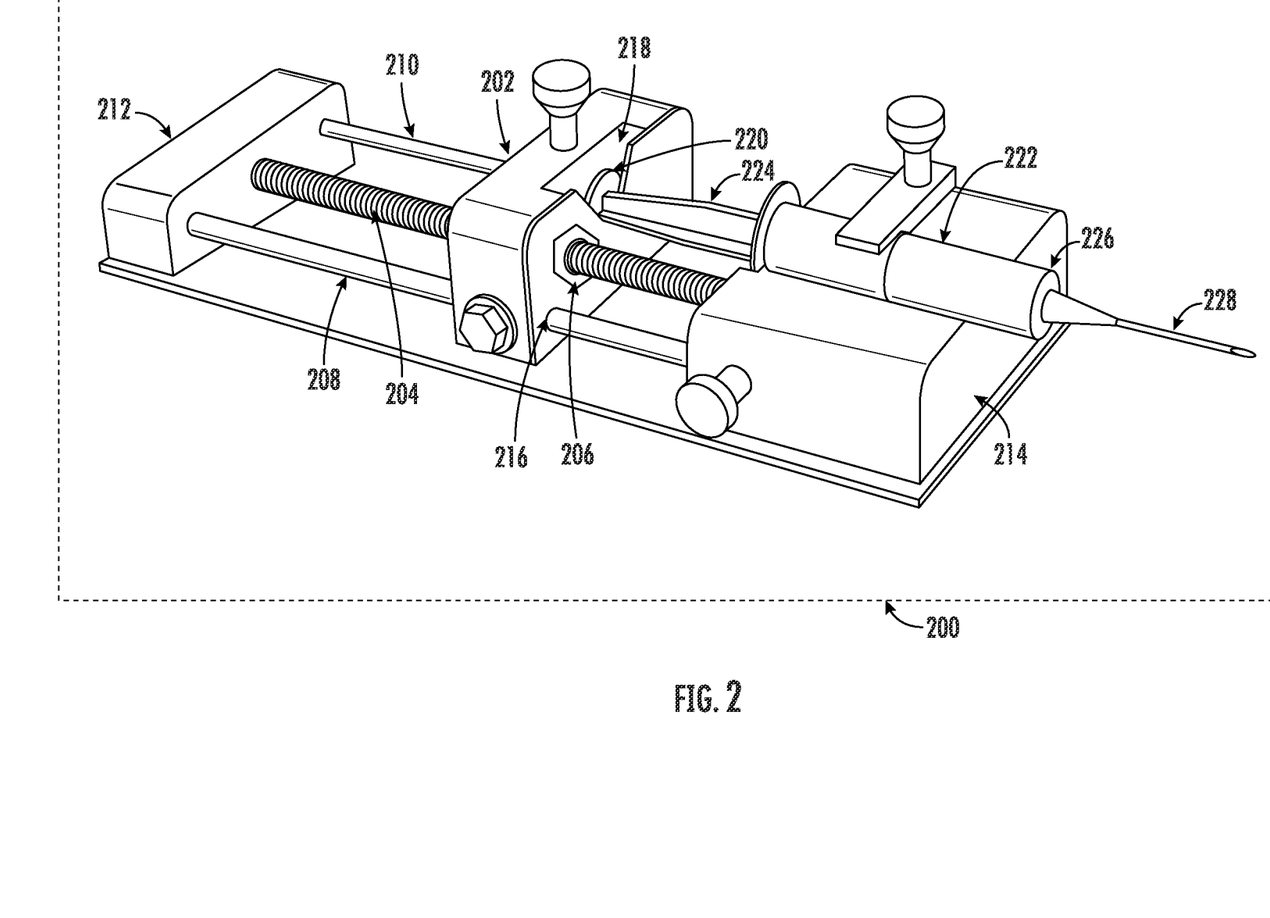
FIG. 2 shows an example illustration in accordance with various embodiments of the present disclosure.

In some embodiments, the example carriage component may be slidably coupled to a rail component. Referring now to FIG. 2, an example illustration 200 shows an example carriage component 202.

Similar to the example carriage component 119 described above in connection with FIG. 1, the example carriage component 202 may be fastened to the example nut component 206. Similar to the example nut component 123 and the example shaft component 125 described above in connection with FIG. 1, the example nut component 206 may comprise inner threads, and the example shaft component 204 may comprises outer threads that engage and mate with the inner threads of the example nut component 206.

In the example shown in FIG. 2, the example carriage component 202 is slidably coupled to a first rail component 208 and a second rail component 210.

In some embodiments, the first rail component 208 may be in the form of a metal tube. In some embodiments, a first end of the first rail component 208 may be secured to a first support stand 212, and a second end of the first rail component 208 may be secured to a second support stand 214. As such, the first rail component 208 may not be movable. In some embodiments, the first rail component 208 may be positioned in a parallel arrangement with the example shaft component 204.

In some embodiments, the second rail component 210 may be in the form of a metal tube. In some embodiments, a first end of the second rail component 210 may be secured to a first support stand 212, and a second end of the second rail component 210 may be secured to a second support stand 214. As such, the second rail component 210 may not be movable. In some embodiments, the second rail component 210 may be positioned in a parallel arrangement with the example shaft component 204.

While the description above provides examples of rail components, it is noted that the scope of the present disclosure is not limited to the description above. In some examples, an example rail component may comprise one or more additional and/or alternative elements, and/or in other shapes or forms.

In the example shown in FIG. 2, the example carriage component 202 comprises one or more through holes (for example, a through hole 216), where one or more rail components may pass through. For example, the first rail component 208 may pass through the through hole 216. As such, the example carriage component 202 may be slidably coupled to and may move along the first rail component 208. Similarly, the example carriage component 202 may be slidably coupled to and may move along the second rail component 210.

Similarly to those described above in connection with FIG. 1, one end of the example shaft component 204 may be coupled to an example motor component, which may exert rotational force on the example shaft component 204. As described above, the example shaft component 204 engages and mates with the example nut component 206 (for example, through threading as discussed above). The example carriage component 202 is fastened to the example nut component 206 and slidably coupled to the first rail component 208 and the second rail component 210 (which are not moveable). The exerted rotational force may cause the outer threads of the example shaft component 204 to rotate, and the example nut component 206 may convert or translate the rotational motion to linear motion as the inner threads of the example nut component 206 engage with the outer threads of the shaft component 204. As such, the example nut component 206 may move along the example shaft component 204, causing the example carriage component 202 to move along the first rail component 208 and the second rail component 210.

In the example shown in FIG. 2, the example carriage component 202 is in contact with the example plunger flange element 220 of the example syringe assembly 222. For example, the example carriage component 202 may comprise a recessed portion 218 on the surface of the example carriage component 202. The recessed portion 218 may be in a shape that corresponds to the shape of the example plunger flange element 220. In the example shown in FIG. 2, the example syringe assembly 222 is secured on a top surface of the second support stand 214 and positioned so that the recessed portion 218 on the surface of the example carriage component 202 is in contact with the example plunger flange element 220 of the example syringe assembly 222. In some embodiments, the example plunger flange element 220 of the example syringe assembly 222 is secured on the recessed portion 218 on the surface of the example carriage component 202, such that the movement of the example carriage component 202 causes the movement of the example plunger flange element 220.

While the description above provides an example relative positional arrangement between the example carriage component and the example syringe assembly, it is noted that the scope of the present disclosure is not limited to the description above. In some examples, the example carriage component and the example syringe assembly may be positioned differently than those shown in FIG. 2.

As described above, when an example motor component exerts rotational force on the example shaft component 204, the example carriage component 202 may move along the first rail component 208 and the second rail component 210. When the example carriage component 202 is in contact with the example plunger flange element 220, the movement of the example carriage component 202 may cause the example plunger component 224 to be pulled or pushed. Similar to those described above in connection with FIG. 1, when the example plunger component 224 is pushed, the example syringe assembly 222 may expel the liquid substance that is stored in the example barrel component 226 through the injection component 228, one end of which may be inserted in an example capillary component.

Referring back to FIG. 1, in accordance with various embodiments of the present disclosure, the example liquid substance vaporization system 100 may comprise an example syringe assembly 107. The example syringe assembly 107 may be configured to inject an example liquid substance 109 to an example capillary component 105. The injection of the example liquid substance 109 may be caused by an example carriage component 119 exerting a push force on the example plunger component 115 of the example syringe assembly 107. As described above, in some embodiments, the example plunger component 115 of the example syringe assembly 107 is coupled or secured to the example carriage component 119, and the example carriage component 119 may receive the force through the example lead screw assembly 121 that is powered by the example motor component 135.

In some embodiments, the example syringe assembly 107 may inject the example liquid substance 109 to the example capillary component 105 at an injection rate. In the present disclosure, the term "injection rate" is defined by the amount or volume of liquid substance being injected to an example capillary component during a time unit (for example, one minute). In some embodiments, the injection rate may be determined based on the rotational speed of the example motor component 135. For example, the faster the rotational speed of the example motor component 135, the faster the injection rate of injecting the example liquid substance 109. The slower the rotational speed of the example motor component 135, the slower the injection rate of injecting the example liquid substance 109.

As described above, the example processing circuitry 137 is in electronic communication with the example motor component 135, and may adjust or control the rotational speed of the example motor component 135. As such, the example processing circuitry 137 may adjust or control the injection rate of injecting the example liquid substance 109 into the example capillary component 105.

Referring back to FIG. 1, in some embodiments, the example vaporization housing 103 may comprise an example input tunnel 139 and an example output tunnel 141.

In some embodiments, the example input tunnel 139 may be in the form of a tube or tubing, such as, but not limited to, a PTFE tubing. The example input tunnel 139 may be disposed on an outer surface of the example vaporization housing 103, and one end of the example input tunnel 139 may be connected to an aperture of the example vaporization housing 103. In some embodiments, the example input tunnel 139 may pass through an aperture on a side or a wall of the example constant temperature chamber 101, as shown in FIG. 1.

In some embodiments, the example input tunnel 139 may be configured to receive a gaseous substance, and may provide a passage for the gaseous substance to enter from outside the example vaporization housing 103 to inside the example vaporization housing 103. Example gaseous substance may include, but not limited to, air, nitrogen, and/or the like. For example, one end of the example input tunnel 139 may be coupled to an example input component 143 that may provide the gaseous substance, such as air.

In some embodiments, the example input component 143 may be in the form of an example air pump component. In such embodiments, the example air pump component is coupled to the example input tunnel 139 of the example vaporization housing 103, and is configured to push air into the example vaporization housing 103 through the example input tunnel 139.

In some embodiments, the example input component 143 may be in the form of an example compressed air storage component. In such embodiments, the example compressed air storage component is coupled to the example input tunnel 139 of the example vaporization housing 103. For example, the compressed air storage component may be an air tank, where compressed air may be stored. In such an example, an opening valve of the air tank may be connected to the one end of the example input tunnel 139. When the opening valve of the air tank is turned on, air may flow from the air tank into the example vaporization housing 103 through the example input tunnel 139. In examples where the example input component 143 is in the form of an example compressed air storage component, the example input tunnel 139 and/or the example output tunnel 141 may comprise at least one decompression aperture (for example, positioned on the tubing of the example input tunnel 139 and/or the example output tunnel 141), such that excessive air pressure from the compressed air storage component may be relieved, and damage to the example vaporization housing 103 due to excessive air pressure may be prevented.

Referring back to FIG. 1, in some embodiments, the gaseous substance received by the input tunnel 139 may flow through the example vaporization housing 103. As described above, the example vaporization housing 103 may comprise the example capillary component 105 disposed within, where the example liquid substance 109 is injected to the example capillary component 105 by the example syringe assembly 107. As described above, the capillary component 105 may expand the surface area of the example liquid substance 109. As the gaseous substance flows through the capillary component 105, the example liquid substance 109 diffused in the example capillary component 105 may be vaporized and become vaporized substance.

In some embodiments, the example output tunnel 141 may be configured to discharge the vaporized substance. In some embodiments, the example output tunnel 141 may be in the form of a tube or tubing, such as, but not limited to, a PTFE tubing. The example output tunnel 141 may be disposed on an outer surface of the example vaporization housing 103, and one end of the example output tunnel 141 may be connected to an aperture of the example vaporization housing 103. In some embodiments, the example output tunnel 141 may pass through an aperture on a side or a wall of the example constant temperature chamber 101, as shown in FIG. 1. In some embodiments, the example output tunnel 141 may provide a passage for the gaseous substance to exit from inside the example vaporization housing 103 to outside the example vaporization housing 103.

In some embodiments, an example flow rate controller component 145 is coupled to the example output tunnel 141 of the example vaporization housing 103. In some embodiments, the example flow rate controller component 145 is configured to measure and/or control the flow rate of gaseous substance and/or vaporized substance that flow through or discharged from the example vaporization housing 103.

For example, the example flow rate controller component 145 may be in the form of a mass flow controller (MFC). In such an example, the MFC may comprise an inlet port, an outlet port, a mass flow sensor and a proportional control valve. The inlet port of the MFC may be connected to the example output tunnel 141 and receive gaseous substance and/or vaporized substance discharged from the example vaporization housing 103. The gaseous substance and/or vaporized substance may flow through the MFC, and a flow rate of the gaseous substance and/or vaporized substance may be measured by the mass flow sensor of the MFC.

In some embodiments, the MFC may be in electronic communication with the example processing circuitry 137, and may provide measurement data (for example, flow rate reading indications) from the mass flow sensor of the MFC to the example processing circuitry 137. The flow rate reading indications may indicate a measured flow rate of the gaseous substance and/or vaporized substance flowing through the MFC.

In some examples, the gaseous substance and/or vaporized substance may flow through the proportional control valve of the MFC, and the example processing circuitry 137 may provide one or more control data (for example, control indications) to the MFC that may cause adjustments of the proportional control valve, which in turn may modify the flow rate of the gaseous substance and/or vaporized substance.

As such, the example processing circuitry 137 may measure, detect, and/or control the flow rate of the gaseous substance and/or vaporized substance flow through the example output tunnel 141 of the example vaporization housing 103.

While the description above provides an example of flow rate controller component, it is noted that the scope of the present disclosure is not limited to the description above. In some examples, an example flow rate controller component may comprise one or more additional and/or alternative elements, and may be positioned differently than the example shown in FIG. 1.

For example, the example flow rate controller component may be coupled to the example input tunnel 139 subsequent to the example input component 143. In such an example, the example input component 143 may provide gaseous substance (such as air) to the flow rate controller component, and the gaseous substance may flow through the example flow rate controller component and enter the example vaporization housing 103 through the example input tunnel 139. Similar to those described above, the example flow rate controller component may be in electronic communication with the example processing circuitry 137, which may in turn control the flow rate of the gaseous substance that flows into the example vaporization housing 103.

Figure 3:
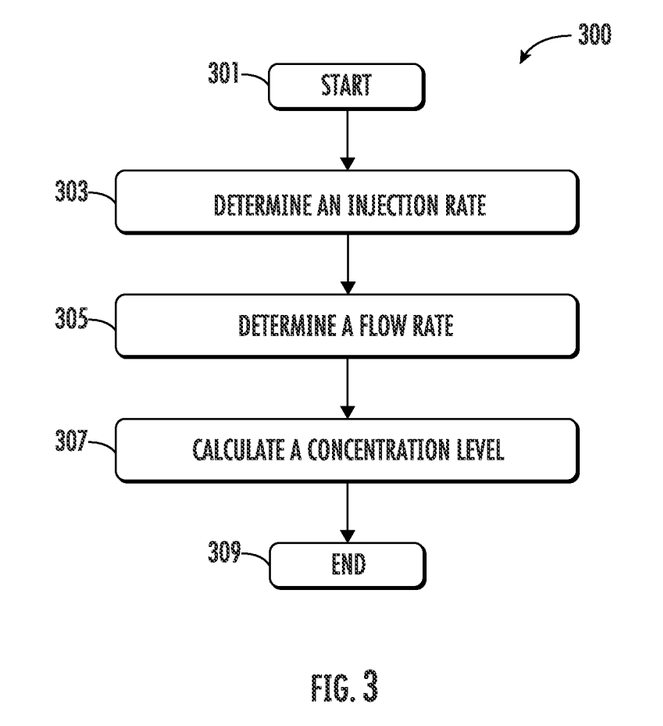
FIG. 3 illustrates an example flow diagram in accordance with various embodiments of the present disclosure.
Figure 4:
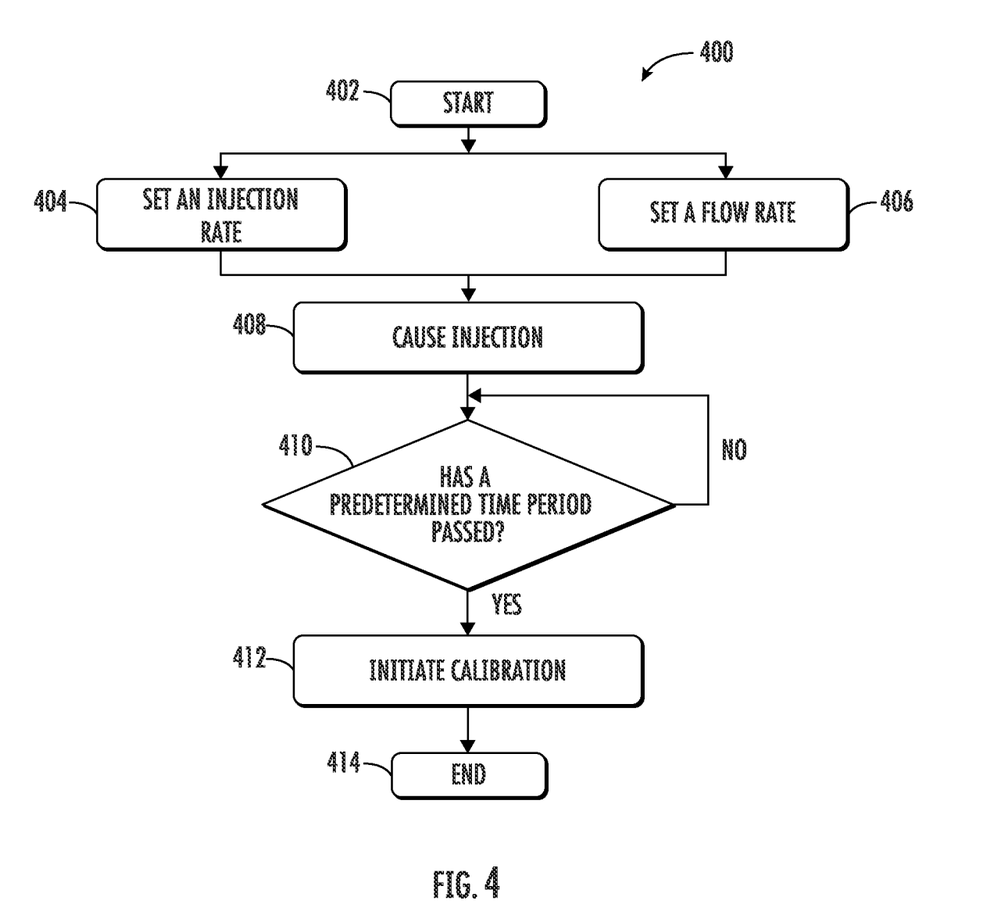
FIG. 4 illustrates an example flow diagram in accordance with various embodiments of the present disclosure.

In accordance with various embodiments of the present disclosure, a concentration level of a vaporized substance may be calculated and/or a predetermined concentration level of a vaporized substance may be produced. Referring now to FIG. 3 and FIG. 4, example flow diagrams illustrating example methods of calculating a concentration level of a vaporized substance and/or producing a vaporized substance having a desired concentration level are shown.

It is noted that each block of the flowchart, and combinations of blocks in the flowchart, may be implemented by various means such as hardware, firmware, circuitry and/or other devices associated with execution of software including one or more computer program instructions. For example, one or more of the procedures described in FIG. 3 and FIG. 4 may be embodied by computer program instructions, which may be stored by a non-transitory memory of an apparatus employing an embodiment of the present disclosure and executed by a processing circuitry in the apparatus. These computer program instructions may direct a programmable apparatus to function in a particular manner, such that the instructions stored in the computer-readable storage memory produce an article of manufacture, the execution of which implements the function specified in the flowchart block(s).

As described above and as will be appreciated based on this disclosure, embodiments of the present disclosure may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Similarly, embodiments may take the form of a computer program code stored on at least one non-transitory computer-readable storage medium. Any suitable computer-readable storage medium may be utilized including non-transitory hard disks, CD-ROMs, flash memory, optical storage devices, or magnetic storage devices.

Referring now to FIG. 3, an example method 300 is illustrated. In particular, the example method 300 illustrates example steps/operations of determining/calculating a concentration level of a vaporized substance in accordance with example embodiments of the present disclosure.

The example method 300 starts at block 301 and then proceeds to step/operation 303. At step/operation 303, a processing circuitry (such as the example processing circuitry 137 described above in connection with FIG. 1) may determine an injection rate of a liquid substance. In some embodiments, the injection rate may indicate a rate of injecting a liquid substance to a capillary component, as described above.

For example, as described above in connection with FIG. 1 and FIG. 2, an example capillary component may be disposed in an example vaporization housing, and may comprise material(s) such as, but not limited to, acetate fiber material, glass fiber material, and/or the like. In some embodiments, the example vaporization housing may be disposed in a constant temperature chamber.

In some embodiments, similar to those described above in connection with FIG. 1 and FIG. 2, an example syringe assembly may comprise an example injection component, and one end of the example injection component is inserted in the example capillary component. The example syringe assembly may also comprise an example barrel component that stores a liquid substance (for example, but not limited to, $H_2O_2$). The example syringe assembly may also comprise an example plunger component configured to expel the liquid substance from the example barrel component through the example injection component to the example capillary component when a push motion is exerted on the example plunger component (for example, on the example plunger flange component). As such, the injection rate for injecting a liquid substance to a capillary component may correlate to the speed of the push motion exerted on the example plunger flange component.

Further, as described above in connection with FIG. 1 and FIG. 2, an example carriage component may be in contact with the example plunger flange component. The example carriage component may be secured to an example lead screw assembly (for example, to an example nut component), which may convert or translate rotational force (or motion) from an example motor component to linear force (or motion). As such, the example carriage component may exert push motion on the example plunger flange component, and the injection rate may correlate to the rotational speed of the example motor component.

As such, in accordance with various examples of the present disclosure, the processing circuitry may determine the injection rate based on the motor speed (for example, the rotational speed) of the example motor component. For example, the processing circuitry may be in electronic communication with the example motor component, and may receive an electronic indication (for example, a signal) indicating a rotational speed of the example motor component. Based on the rotational speed, the processing circuitry may determine the injection rate.

Referring back to FIG. 3, subsequent to step/operation 303, the method 300 proceeds to step/operation 305. At step/operation 305, a processing circuitry (such as the example processing circuitry 137 described above in connection with FIG. 1) may determine a flow rate of a gaseous substance in the example vaporization housing. In some embodiments, the gaseous substance is for vaporizing the liquid substance in the vaporization housing. In some embodiments, the gaseous substance is air.

In some embodiments, similar to those described above in connection with FIG. 1 and FIG. 2, the flow rate is measured based on a rate of providing a gaseous substance to the example vaporization housing through an input tunnel of the example vaporization housing. For example, as described above, an example flow rate controller component may be coupled to the input tunnel of the example vaporization housing. The example flow rate controller may generate a flow rate reading indication that indicates a measured flow rate. The example flow rate controller component may be in electronic communication with the processing circuitry, and the processing circuitry may receive the flow rate reading indication from the flow rate controller component.

In some embodiments, similar to those described above in connection with FIG. 1 and FIG. 2, the flow rate is measured based on a rate of a gaseous substance or vaporized substance discharged from the example vaporization housing through an output tunnel of the example vaporization housing. For example, as described above, an example flow rate controller component may be coupled to the output tunnel of the example vaporization housing. The example flow rate controller may generate a flow rate reading indication indicating a flow rate. The example flow rate controller component may be in electronic communication with the processing circuitry, and the processing circuitry may receive the flow rate reading indication from the flow rate controller component.

Referring back to FIG. 3, subsequent to step/operation 305, the method 300 proceeds to step/operation 307. At step/operation 307, a processing circuitry (such as the example processing circuitry 137 described above in connection with FIG. 1) may calculate a concentration level. In some embodiments, the concentration level may correspond to a concentration level of a vaporized substance. For example, the vaporized substance may be a substance that has vaporized from a liquid state (for example, the liquid substance injected to the example capillary component) to a gaseous state in the example vaporization housing.

As an example, the barrel component of the example syringe assembly may store liquid $H_2O_2$, and the liquid $H_2O_2$ may be injected to the example capillary component such that a surface of the liquid $H_2O_2$ may be expanded. As the gaseous substance (for example, air) flow through the example vaporization housing, the liquid $H_2O_2$ in the example capillary component may vaporize into gaseous $H_2O_2$. The gaseous $H_2O_2$, mixed with other gaseous substance (e.g. air), may be discharged from the example vaporization housing, and the processing circuitry may determine a concentration level of the gaseous $H_2O_2$ in the mixed gaseous substance.

In some embodiments, the processing circuitry may determine a concentration level of the vaporized substance based at least in part on the injection rate and the flow rate. For example, the processing circuitry may calculate the concentration level based on the following formula:

$$C_v = \frac{R_i \times k_i}{(R_f \times k_f) + (R_i \times k_i)}$$

In the above formula, $C_v$ represents the concentration level of the vaporized substance (for example, the amount of $H_2O_2$ molecules as a percentage value to the total amount of molecules in the mixed gaseous substance discharged from the vaporization housing). $R_i$ represents an injection rate (for example, a volume of injecting the liquid $H_2O_2$ to the capillary component per minute). $k_i$ represents a liquid substance concentration level (for example, the amount of $H_2O_2$ molecules in the liquid $H_2O_2$ concentration per liter). $R_f$ represents a flow rate (for example, a volume of air flowing through the vaporization housing per minute). $k_f$ represents a gaseous substance concentration level (for example, the amount of molecules in the air per liter). In some embodiments, the values of $k_i$ and/or $k_f$ may be predetermined.

While the description above provides an example formula for calculating the concentration level of the vaporized substance, it is noted that the scope of the present disclosure is not limited to the description above. In some examples, an example method may calculate the concentration level based on one or more additional and/or alternative formulas.

Referring back to FIG. 3, subsequent to step/operation 307, the method 300 proceeds to block 309 and ends.

Referring now to FIG. 4, an example method 400 is illustrated. In particular, the example method 400 illustrates example steps/operations of setting the injection rate and the flow rate to produce vaporized substance that has a desired concentration level.

The example method 400 starts at block 402 and then proceeds to step/operation 404. At step/operation 404, a processing circuitry (such as the example processing circuitry 137 described above in connection with FIG. 1) may set an injection rate for injecting the liquid substance to the example capillary component.

Similar to those described above in connection with FIG. 3, the injection rate may correlate to the rotational speed of the example motor component. As such, the processing circuitry may set the injection rate by transmitting control indications to the example motor component that indicates the rotational speed of the example motor component.

At step/operation 406, a processing circuitry (such as the example processing circuitry 137 described above in connection with FIG. 1) may set a flow rate of a gaseous substance flowing into or out of the vaporization housing. In some embodiments, the gaseous substance is for vaporizing the liquid substance in the vaporization housing. In some embodiments, the gaseous substance is air.

Similar to those described above in connection with FIG. 3, the processing circuitry may be in electronic communication with the example flow rate controller component. The flow rate controller component may comprise proportional control valve, which may modify the flow rate of the gaseous substance (and/or vaporized substance) flowing into (or out of) the vaporization housing. The processing circuitry may provide one or more control indications to the example flow rate controller component, which may cause adjustments of the proportional control valve and in turn set the flow rate of a gaseous substance flowing into (or out of) the vaporization housing.

In some embodiments, the processing circuitry may set the value for the injection rate and/or the value for the flow rate based on the desired concertation level of the vaporized substance. For example, the value for the injection rate and/or the value for the flow rate may be determined based on the formula described above in connection with step/operation 307 of FIG. 3.

In some embodiments, the injection rate may be within a range between 0.01 microliter per minute and 1 milliliter per minute. In some embodiments, the inject rate may be 0.3 microliter per minute. In some embodiments, the inject rate may be within other range(s) and/or of other value(s).

In some embodiments, the flow rate may be within a range between 100 milliliter per minute and 2 liter per minute. In some embodiments, the flow rate may be 1500 milliliter per minute. In some embodiments, the flow rate may be within other range(s) and/or of other value(s).

In different embodiments, the step/operation 404 and the step/operation 406 may be performed in different sequences. In some embodiments, the step/operation 404 may be performed prior to the step/operation 406. In some embodiments, the step/operation 404 may be performed subsequent to the step/operation 406. In some embodiments, the step/operation 404 and the step/operation 406 may be performed simultaneously.

Referring back to FIG. 4, subsequent to step/operation 404 and/or step/operation 406, the method 400 proceeds to step/operation 408. At step/operation 408, a processing circuitry (such as the example processing circuitry 137 described above in connection with FIG. 1) may cause injection of the liquid substance to the capillary component.

For example, the processing circuitry may trigger the example motor component to start operating. The motor component may be coupled to a shaft component and configured to exert rotational force on the shaft component. The shaft component may comprise outer threads that engage with inner threads of a nut component, and the nut component may convert or translate the rotational force to linear force. A carriage component may be fastened to the nut component and slidably coupled to a rail component. Due to the linear force, the carriage component may move along the rail component, and may convey the force to a plunger flange element of a syringe assembly, causing the syringe assembly to inject liquid substance stored in a barrel component of the syringe assembly to the capillary component.

Referring back to FIG. 4, subsequent to step/operation 408, the method 400 proceeds to step/operation 410. At step/operation 410, a processing circuitry (such as the example processing circuitry 137 described above in connection with FIG. 1) may determine whether a predetermined time period has passed since injecting the liquid substance at step/operation 408.

In some embodiments, the predetermined time period is predetermined as the amount of time necessary for vaporization of the liquid substance to be stable. In some embodiments, the predetermined time period is 30 minutes. In some embodiments, the predetermined time period may be of other length(s) of time.

If, at step/operation 410, the processing circuitry determines that the predetermined time period has not passed, the method 400 may return to step/operation 410 and the processing circuitry may stay idle until the predetermined time period has passed.

If, at step/operation 410, the processing circuitry determines that the predetermined time period has passed, the example method 400 proceeds to step/operation 412. At step/operation 412, a processing circuitry (such as the example processing circuitry 137 described above in connection with FIG. 1) may initiate calibration of a substance sensing component (for example, a gas detector).

In some embodiments, the substance sensing component may receive the vaporized substance (e.g. vaporized $H_2O_2$) in accordance with various embodiments of the present disclosure. For example, the substance sensing component may be coupled to the output tunnel of the vaporization housing and/or coupled to the outlet port of the flow rate controller component. As described above, the concentration level of the vaporized substance (e.g. vaporized $H_2O_2$) may be calculated based on the injection rate and the flow rate, and the concentration level may be factored in when calibrating the substance sensing component, as described above.

Figure 5:
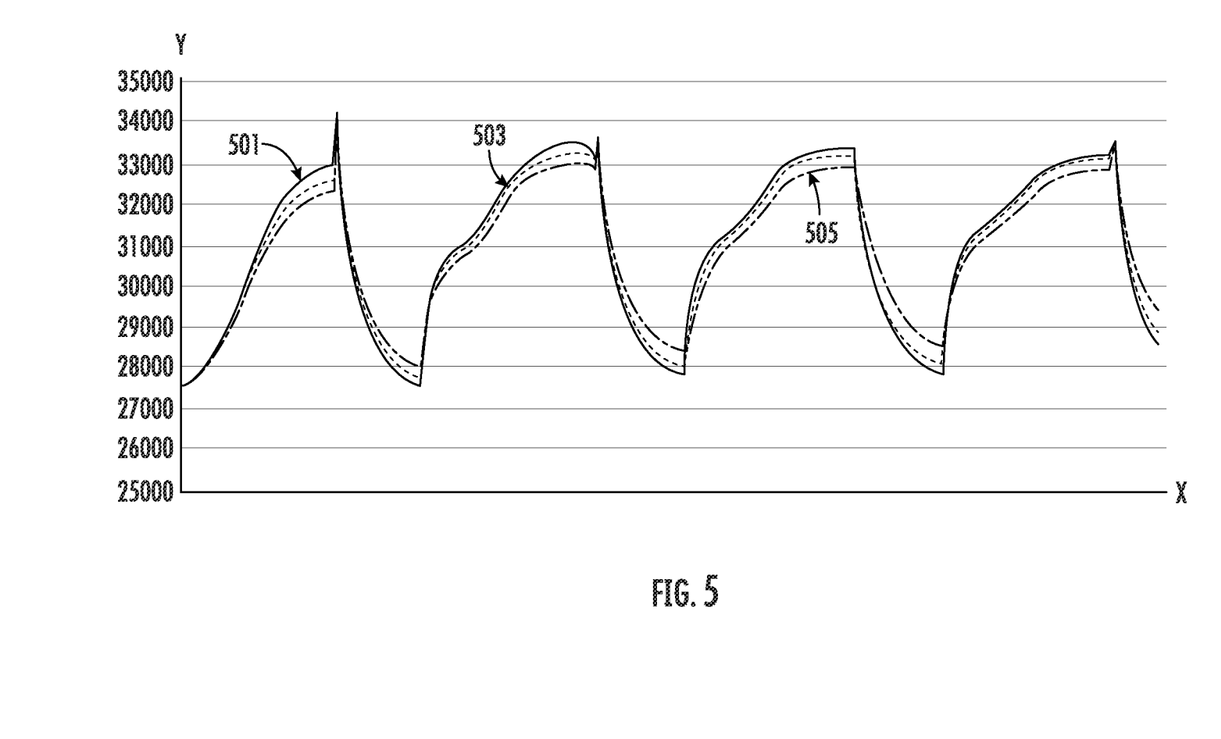
FIG. 5 illustrates an example graph in accordance with various embodiments of the present disclosure.

Referring now to FIG. 5, an example graph is shown. The X-axis of the example graph represents different calibration points (for example, each calibration point may correspond to a given injection rate and a given flow rate). The Y-axis of the example graph represents concentration levels of vaporized substance that are produced in accordance with examples of the present disclosure. In FIG. 5, each of the curve 501, the curve 503, and the curve 505 represents data obtained from calibrating one substance sensing component. In particular, the curve 501, the curve 503, and the curve 505 are plotted based on the concentration level of vaporized substance produced in accordance with examples of the present disclosure at different calibration points. As shown in FIG. 5, the curve 501, the curve 503, and the curve 505 may substantially overlap with one another, indicating that various examples of the present disclosure may repeatably and reliably produce vaporized substance having desired concentration levels, therefore may overcome technical challenges and difficulties faced by many other systems as described above.

Referring back to FIG. 4, subsequent to step/operation 412, the method 400 proceeds to block 414 and ends.

It is to be understood that the disclosure is not to be limited to the specific embodiments disclosed, and that modifications and other embodiments are intended to be included within the scope of the appended claims. Although specific terms are employed herein, they are used in a generic and descriptive sense only and not for purposes of limitation, unless described otherwise.

The invention claimed is:

1. An apparatus for vaporizing a liquid substance comprising:
   a constant temperature chamber comprising a vaporization housing, wherein a capillary component is disposed in the vaporization housing; and
   a syringe assembly configured to inject the liquid substance to the capillary component to vaporize the liquid substance within the capillary component; wherein the vaporization housing comprises an input tunnel and an output tunnel, wherein the input tunnel is configured to receive a gaseous substance, wherein the output tunnel is configured to discharge the vaporized substance.

2. The apparatus of claim 1, wherein the syringe assembly comprises an injection component, a barrel component, and a plunger component, wherein a first end of the injection component is inserted in the capillary component, wherein the barrel component stores the liquid substance, wherein the plunger component comprises a plunger flange element.

3. The apparatus of claim 2, further comprising:
   a carriage component in contact with the plunger flange element; and
   a lead screw assembly coupled to the carriage component.

4. The apparatus of claim 3, wherein the lead screw assembly comprises:
   a nut component having inner threads; and
   a shaft component having outer threads that engage with the inner threads of the nut component;
   wherein the carriage component is fastened to the nut component and slidably coupled to a rail component.

5. The apparatus of claim 4, wherein the lead screw assembly comprises:
   a motor component coupled to the shaft component and configured to exert rotational force on the shaft component; and
   a processing circuitry in electronic communication with the motor component.

6. The apparatus of claim 1, further comprising:
   an air pump component coupled to the input tunnel of the vaporization housing;
   a flow rate controller component coupled to the output tunnel of the vaporization housing; and
   a processing circuitry in electronic communication with the flow rate controller component.

7. The apparatus of claim 1, further comprising:
   a compressed air storage component coupled to the input tunnel of the vaporization housing;

a flow rate controller component coupled to the output tunnel of the vaporization housing, wherein the output tunnel comprises at least one decompression aperture; and a processing circuitry in electronic communication with the flow rate controller component.

8. The apparatus of claim 1, wherein the capillary component comprises acetate fiber material.

9. The apparatus of claim 1, wherein the capillary component comprises glass fiber material.

10. The apparatus of claim 1, wherein the capillary component comprises paper material.

11. A method for determining a concentration level of a vaporized substance comprising:

determining an injection rate of injecting a liquid substance by a syringe assembly to a capillary component, wherein the capillary component is disposed in a vaporization housing, wherein the liquid substance is injected to the capillary component to vaporize the liquid substance within the capillary component;

determining a flow rate of a gaseous substance for vaporizing the liquid substance in the vaporization housing; and calculating the concentration level of the vaporized substance based on the injection rate and the flow rate.

12. The method of claim 11, further comprising:

causing the syringe assembly to inject the liquid substance to the capillary component, wherein the syringe assembly comprises an injection component, a barrel component storing the liquid substance, and a plunger component comprising a plunger flange element, wherein a first end of the injection component is inserted in the capillary component.

13. The method of claim 12, wherein the plunger flange element is in contact with a carriage component, wherein the carriage component is coupled to a lead screw assembly.

14. The method of claim 13, wherein the lead screw assembly comprises a nut component having inner threads and a shaft component having outer threads that engage with the inner threads of the nut component, wherein the carriage component is fastened to the nut component and slidably coupled to a rail component.

15. The method of claim 14, wherein the lead screw assembly comprises a motor component coupled to the shaft component and configured to exert rotational force on the shaft component.

16. The method of claim 15, wherein determining the injection rate of injecting the liquid substance further comprises:

determining a motor speed of the motor component.

17. The method of claim 11, wherein determining the flow rate of the gaseous substance further comprises:

receiving a flow rate reading indication from a flow rate controller component coupled to an output tunnel of the vaporization housing.

18. The method of claim 11, wherein the vaporization housing is disposed in a constant temperature chamber.

19. The method of claim 11, wherein the capillary component comprises acetate fiber material.

20. The method of claim 11, wherein the capillary component comprises glass fiber material.

* * * * *